(12) United States Patent
Ghislain

(10) Patent No.: US 8,253,946 B2
(45) Date of Patent: *Aug. 28, 2012

(54) SENSOR APPARATUS AND METHOD USING OPTICAL INTERFEROMETRY

(75) Inventor: Lucien P. Ghislain, Millbrae, CA (US)

(73) Assignee: Lucien P. Ghislain, Millbrae, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/928,736

(22) Filed: Dec. 16, 2010

(65) Prior Publication Data
US 2011/0164254 A1 Jul. 7, 2011

Related U.S. Application Data

(63) Continuation of application No. 12/586,475, filed on Sep. 21, 2009, now Pat. No. 7,880,893.

(51) Int. Cl.
*G01B 9/02* (2006.01)

(52) U.S. Cl. .................................................... 356/480

(58) Field of Classification Search ................. 356/480, 356/477, 478, 506, 519
See application file for complete search history.

(56) References Cited

U.S. PATENT DOCUMENTS

2003/0112443 A1 * 6/2003 Hjelme et al. ............... 356/480
* cited by examiner

*Primary Examiner* — Tarifur Chowdhury
*Assistant Examiner* — Jonathan Cook
(74) *Attorney, Agent, or Firm* — Lumen Patent Firm

(57) ABSTRACT

A sensor includes a sensor head with at least two surfaces separated by a gap. One surface is mechanically fixed, a second surface is free to move and deflections of the second surface relative to the first surface are monitored by optical interferometry. An optical fiber could be used to direct light from a light source to the sensor and collect light reflected by the sensor. Interaction of molecules or other objects in the sample with the second surface is detected as a change in amplitude and/or phase of deflection the second surface in response to an applied driving signal. A layer of binding molecules may be immobilized on the second surface and this surface exposed to a sample.

18 Claims, 10 Drawing Sheets

SENSOR APPARATUS AND METHOD USING OPTICAL INTERFEROMETRY

CROSS-REFERENCE TO RELATED APPLICATIONS

This application is a continuation of U.S. patent application Ser. No. 12/586,475 filed Sep. 21, 2009 now U.S. Pat. No. 7,880,893, which is incorporated herein by reference.

FIELD OF THE INVENTION

The invention relates to an apparatus and method for detecting the presence, amount, or rate of binding of one or more analytes in a sample, and in particular, to apparatus and method using optical interferometry to monitor displacement of a sensor element.

BACKGROUND OF THE INVENTION

High sensitivity, real-time, label-free monitoring of binding to a surface in a liquid, in a gaseous environment, or in a vacuum has a wide range of applications, including thin film thickness monitoring during deposition, biological applications for molecular, viral, bacterial and cellular detection, surface science, surfactant research, drug research and discovery, electrochemistry (including plating and etching) and in situ monitoring (eg. oil condition).

Diagnostic tests based on a binding event between members of binding pair are widely used in medicine, agriculture, food analysis and research. These tests are designed to detect the presence, amount, rate of binding of a wide variety analytes. Typical binding pairs include antibody-antigen, receptor-ligand, DNA or RNA hybridizing pairs.

In a solid-phase assay molecules are immobilized on a solid surface, the solid surface is exposed to a sample under conditions that promote binding, binding occurs in a defined detection zone, and binding events may be detected by a variety of direct and indirect methods. Methods of direct detection include a change in mass, viscosity, elasticity, dissipation, electric charge or potential, surface stress, reflectivity, thickness, color. Methods of indirect detection include the use of a chromophore or fluorescent label, and radiolabels. Further, binding can be detected after it occurs by a secondary fluorescent-labeled anti-analyte antibody.

Prior art U.S. Pat. No. 5,804,453, "Fiber optic direct-sensing bioprobe using a phase-tracking approach" issued to Chen; Duan-Jun, and related U.S. Application No. 20050254062 "Fiber-optic assay apparatus based on phase-shift interferometry" issued to H. Tan et al. discloses an optical fiber interferometer assay device that is designed for direct detection of binding to an optical fiber end surface. Detection is based on a change in thickness at the optical fiber end surface due to molecular binding. The change in thickness changes an optical interference signal due to the phase shift between light reflected from two layers on the optical fiber end surface: a first layer and a second layer that is directly exposed to the, sample. The prior art optical fiber interferometer analyzes the phase shift between the first and second layers using an optical spectrometer operating with visible light in the range 450-700 nm. The phase shift due to binding is detected by changes in the reflected light spectrum over a range of wavelengths, specifically, changes in the peaks and valleys of the reflected light optical spectrum.

One limitation of the prior art optical fiber interferometer is the relatively low sensitivity.

The measured phase shift depends on a change in refractive index and the change in refractive index due to binding of the analyte molecules is extremely small. As a result a large number of molecules are needed to produce a detectable signal. In addition, small changes in the positions of peaks and valleys in the optical spectrum are difficult to detect, and the signal may be weak and buried in noise.

Prior art U.S. Pat. No. 6,436,647, "Method for detecting chemical interactions between naturally occurring biological analyte molecules that are non identical binding partners" issued to Quate, C. F. et al. discloses a method of using cantilevers as sensors for detecting chemical interactions between naturally occurring bio-polymers which are non-identical binding partners. The method is useful whether the reactions occur through electrostatic forces or other forces. Induced stress, heat, or change in mass is detected where a binding partner is placed on a cantilever for possible reaction with analyte molecules (i.e., a non-identical binding partner). The method is particularly useful in determining DNA hybridization but may be useful in detecting interaction in any chemical assay.

Also, prior art U.S. Pat. No. 6,289,717, "Micromechanical antibody sensor", issued to Thundat et al. discloses a sensor apparatus using a microcantilevered spring element having a coating of a detector molecule such as an antibody or antigen. A sample containing a target molecule or substrate is provided to the coating. The spring element bends in response to the stress induced by the binding which occurs between the detector and target molecules. Deflections of the cantilever are detected by a variety of detection techniques. The microcantilever may be approximately 1 to 200 .mu.m long, approximately 1 to 50 .mu.m wide, and approximately 0.3 to 3.0 .mu.m thick. Sensitivity for detection of deflections is in the range of 0.01 nanometers.

One disadvantage of cantilever deflection based sensors is relatively low sensitivity due to the fact that a detectable cantilever deflection is caused by the cumulative effect of the binding of a large number of molecules to a cantilever surface. This can take a significant amount of time, and therefore the sensor response may be relatively slow. Further, the slow response leaves the sensor susceptible to a variety of noise sources (drift, thermal noise). In addition, the cantilever is a relatively rigid free-standing element, rather like a swimming pool diving board and as a result, the surface mass density of typical cantilever sensors is much greater than the surface mass density of the molecules bound to its surface.

In addition, the cantilever sensor has an inconvenient form factor. Cantilever sensors may require an optical alignment each time they are replaced. This is generally inconvenient and particularly inconvenient in the case of multiple cantilever sensors forming an array. Further, cantilever sensors may be too expensive for operation as a single-use disposable, and re-use over many cycles may be difficult to achieve.

U.S. Pat. No. 5,807,758, "Chemical and biological sensor using an ultra-sensitive force transducer", issued to Lee et al. discloses a method and apparatus for detecting a target species. The target molecule may be in liquid phase (in solution) or (for some embodiments of the invention) in vapor phase. A sensor according to the present invention monitors whether a target species has selectively bound to groups on the cantilever surface by monitoring the displacement of the cantilever, and hence the force acting on the cantilever. This force acting on the cantilever arises from the force acting on a structure that moves in electric or magnetic field, and that may be selectively bound to the cantilever. In the case of target species having a sufficiently large net electric charge or dipole moment, the target species itself may serve as the structure that moves in an electric field. More typically however, separate modified structures, such as modified magnetic beads or modified beads having a net charge or a dipole moment, will, when selectively bound to the cantilever, exert a force on the cantilever that relates to the presence of the target species.

This is a cantilever-based approach that has the additional disadvantage of requiring a label and thus it provides only an indirect measure of analyte binding.

U.S. Application No. 20040096357, "Composite sensor membrane", issued to Majumdar et al. discloses a sensor including a membrane to deflect in response to a change in surface stress, where a layer on the membrane is to couple one or more probe molecules with the membrane. The membrane may deflect when a target molecule reacts with one or more probe molecules.

This is a membrane sensor that operates on the same principle the cantilever sensors to detect analyte binding by changes in surface stress. It has the disadvantages of the cantilever sensors as previously described. Specifically, the sensitivity may be relatively low because it requires a large number of binding events. The sensor response may be relatively slow and is generally susceptible to noise and drift. In addition, the membrane is a relatively rigid free-standing element and the surface mass density of the membrane may be much greater than the surface mass density of the molecules bound to its surface. Further, the membrane sensor may be too expensive to be a single-use disposable, and re-use over many cycles may be difficult to achieve.

A related sensor, the quartz crystal microbalance (QCM) is an electro acoustic method suitable for mass and viscoelastic analysis of adsorbed protein layers at the solid/water interface. A typical QCM sensor consists of a megahertz piezoelectric quartz crystal sandwiched between two gold electrodes. The crystal can be brought to resonant oscillation, and shear motions by means of A/C current between the electrodes. Since the resonant frequency (f) can be determined with very high precision, usually less than 1 Hz, the adsorbed mass at the QCM-surface can be detected, or "balanced", down to a few ng/cm2. It has also been shown that there is linear relation between the adsorbed rigid mass and the change in f, in an ideal air/solid situation.

U.S. Pat. No. 6,006,589 "Piezoelectric crystal microbalance device", issued to Rodahl et al. discloses a device and a process for measuring resonant frequency and dissipation factor of a piezoelectric resonator. After exciting the resonator to oscillation, the driving power to the oscillator is turned off after the decay of the oscillation of the resonator is recorded and used to give a measure of at least one of the resonators properties, such as dissipation factor, changes in the dissipation factor, resonant frequency and changes in the resonant frequency. The invention allows these measurements to be performed at either the fundamental resonant frequency or one (or more) of the overtones. The device and the process disclosed herein may be used in a variety of applications such as, for example, measurement of phase transitions in thin films, the detection of adsorption of biomolecules, and measurements of the viscoelastic properties of thin films.

The crystal microbalance sensor typically vibrates in a shear mode with an amplitude of about 1 nm at a fundamental resonant frequency given by:

$$f_{res} \sim 1/d$$

where d is the thickness of the quartz plate. For example, if d is 0.17 mm, the resonance frequency is approximately 10 MHz. The quartz sensor starts to oscillate if an AC electric field with a frequency centered close to the fundamental resonant frequency of the sensor is applied perpendicularly to its surfaces. Usually, electrodes on each side of the sensor plate are deposited by evaporation and are subsequently contacted to an external AC field generator (for example to a signal generator, or to an oscillator drive circuit, or the like). Under favorable conditions this arrangement is capable of sensing mass changes smaller than 1 ng/cm^2.

Ideally the mass changes at the sensor electrode(s) induce a shift in the resonance frequency of the sensor, proportional to the mass changes:

$$\Delta M = -C \Delta f_{res}$$

where C, the proportionality constant, depends on the thickness of the quartz plate.

This relation is valid provided that the mass is attached rigidly to the electrode and follows the oscillatory motion of the sensor without dissipative losses. The relation may fail when the added mass is viscous or is not rigidly attached to the electrode(s) and can thus suffer elastic or plastic deformation(s) during oscillations. The relation between added mass and the shift of the resonant frequency then becomes more complex. The latter situation arises when for example a water droplet is deposited onto an electrode of the quartz sensor.

The Sauerbrey equation describes the linear relation between frequency changes and changes in mass for thin films adsorbing to the crystal microbalance sensor surface. It gives a good estimation of film thickness, as long as the dissipation is relatively low. When the dissipation value reaches above $1 \times 10^{-6}$ per 5 Hz, the film is too soft to function as a fully coupled oscillator. A calculated thickness value will hence be somewhat less than the true value.

Proteins at the water/QCM surface interface can also be quantified with resonance frequency determination, but adsorbed protein layers also have some degree of structural flexibility or viscoelasticity, that are invisible to a simple resonance frequency determination. Viscoelasticity can, however, be visualized by measuring the energy loss, or dissipation (D) of the shear movement of the crystal in water. A new principle of measuring D is to drive the crystal with A/C current at the resonant f followed by disconnection and analysis of the resulting damped sinusoidal curve. This development of pulse assisted discrimination of resonance frequency and dissipation makes QCM analysis of adsorbed protein layers very simple and gives unique information about the hydrodynamic conductivity of the adsorbed protein layers and surrounding water. Very small structural and orientation changes of an adsorbed protein layer, including chemical cross-linking, may be monitored with high accuracy.

One disadvantage of this approach is the piezoelectric crystal sensor size—typically 10-30 mm diameter and 0.1-0.5 mm thickness. Also, the entire sensor element including piezoelectric crystal and electrodes is typically thrown out after each use. In some cases, the sensor element can be reused a number of times, but this requires careful cleaning. In addition, sensor size limits scalability to an array-sensing format for multiple analytes.

A preferred embodiment of the sensor apparatus of the invention includes an optical-fiber based interferometer to measure small displacements. One such interferometer is disclosed in U.S. Pat. No. 5,017,010, "High sensitivity position sensor and method", issued to Mamin et al. This is a highly sensitive apparatus for sensing the position of a movable member comprises an optical directional coupler providing four external ports. Light from a short coherence length diode laser is injected into the first port. The coupler serves as a beam splitter to direct one portion of the injected light to the member via the second port and a single mode optical fiber. Part of this one portion is reflected concurrently from the member and from the adjacent polished coating at the end face of said fiber back into said fiber and optically coupled via the third port to a photodetector to provide a signal whose amplitude is indicative of the position of the member, based upon the relative phase of said concurrent reflections. The other portion of the injected light is optically coupled to and via the fourth port to another photodetector for providing, as a reference, a signal proportional to the intensity of the injected light. These two signals are supplied to a subtractive circuit for providing an output in which power fluctuations of the laser are minimized.

Another embodiment of the invention uses a laser-diode based interferometer for direct sensing of small displacements. One such laser-diode based interferometer is disclosed in U.S. Pat. No. 5,189,906, "Compact atomic force microscope", issued to Sarid et al. This is an atomic force microscope using a laser diode and optical interference of light reflected back into the laser to measure the vertical position of a sensing tip wherein the sensing tip can be either off the sample surface and vibrated where changes in the amplitude of vibration near the natural frequency of the cantilever are used as a measure of changes of electric or magnetic force on the sensing tip; or, the sensing tip can be placed on the sample surface with no vibration to measure directly the profile of the sample surface.

SUMMARY OF THE INVENTION

The invention includes an apparatus for high sensitivity, real-time, label-free monitoring of binding to a surface in a liquid, in a gaseous environment, or in a vacuum. The invention also includes an apparatus for detecting an analyte in a sample, including detecting the presence of analyte, the amount of analyte or the rate of association and/or dissociation of the analyte with a binding partner.

In a preferred embodiment the apparatus includes: a sensor head with at least two surfaces separated by a gap. The first surface may be mechanically fixed, for example, a reflective layer coated on an optical fiber end surface. The second surface may be free to move, for example a membrane or diaphragm capable of reflecting light and supported over the circumference but otherwise free to move. A layer of binding molecules immobilized on the second surface is exposed to a sample. A light source generating light that is directed to the reflecting surfaces and a light detector monitoring the light reflected by the reflecting surfaces.

The apparatus may also include a driving signal generator capable of generating pressure waves in the sample with selectable frequency and amplitude ranging from acoustic to ultrasonic frequencies (from 1 Hz to 1 GHz). The driving signal generator may be formed from any of a wide variety of actuating elements, including: a piezo-electric devices (for example PZT, PVDF, quartz), magnetically driven elements, electrically driven elements (using electrostatic forces or an electric current), thermally driven elements (for example, a resistive heating element), optically driven elements. The pressure wave generator may be mounted separately from the sensor head or may be included as a component of the sensor head.

Alternatively, the second surface may be driven directly by use of actuating elements on or near the sensor head similar to those described above and including: a piezo-electric devices (for example PZT, PVDF, quartz), magnetically driven elements, electrically driven elements (using electrostatic forces or an electric current), thermally driven elements (for example, a resistive heating element), optically driven elements. For example, a surface coated with a magnetic film respond to an applied external magnetic field. Electrostatic forces can deflect the second surface in response to an applied voltage when electrodes are included on or near the two sensor surfaces. In addition, the spacer layer sandwiched by the first and second surfaces may be formed from a piezo-electric material with suitable electrodes. A voltage applied to the electrodes can drive a displacement of the second surface.

In one embodiment, the second surface moves in response to pressure waves in the sample and this motion is monitored as a change in the signal from the light detector.

More specifically, the light source generates light that illuminates the first and second surfaces and the light detector operates to monitor light reflected by the two surfaces. Interference between the two reflected light beams provides a measure of the relative position of the two surfaces. When the second surface moves there is a shift in the phase of the reflected light relative to the light reflected by the first surface. This phase shift changes the light intensity monitored by the light detector. When the sensor head is exposed to the sample, molecules or other objects in the sample can bind to the second surface, and this is detectable as a change in the motion of the second surface in response to an applied pressure wave or driving signal.

The sensor may detect the binding of a wide variety of analytes in a fluid sample, including: antibodies, antigen molecules, protein molecules for detecting binding partners, protein molecules for detecting protein complexes, DNA strands capable of hybridization. The sensor may also detect binding of particles, virus capsids, cells and larger objects of interest. In addition the sensor may detect a variety of analyte in a vapor (gas-phase, or both liquid and vapor phase) sample, including: volatile molecules, compounds and contaminants. Further, the sensor may operate in vacuum to detect the deposition a sample on the sensor surface or collision (with or without binding) of a sample with the sensor surface.

The sensor can also operate without the use of an external driving signal generator. For example, movement of the second surface could be generated by a sample including motile cells (for example, sperm and bateria). Further, movement could be generated by sample particles, molecules, cellular components or even whole cells and larger objects carried by fluid flow in or around the sensor head.

In one particular design the two reflecting surfaces are separated by an air gap. The sensor head may be exposed to a liquid sample with one side of the second surface exposed to the liquid and with an air-gap maintained on the second side in the space between the first and second surfaces.

In another design the two reflecting surfaces are separated by a gap that is directly exposed to the sample (vapor or liquid), and one or both sides of the second surface may be exposed to the sample.

The second surface may be a diaphragm or membrane, a ribbon or strip, a perforated membrane having a pattern of holes, a reflecting surface supported by one or more flexible arms The overall size of the first and second surfaces can be selected for optimum sensitivity. For example, in the case of a membrane or diaphragm the diameter may be in the range 10 cm (10-1 meters) down to 10 nm (10-8 meters), with smaller sizes tending to provide higher sensitivity and faster response times.

The light source can include an optical fiber for directing light to the sensor head and the sensor apparatus further includes an optical coupling for directing reflected light to the light detector.

In a first embodiment, the sensor head is fixedly mounted to an optical fiber with the first reflecting surface in direct contact with the optical fiber end surface.

In a second embodiment, the sensor head is removably attached to the optical fiber and another optical element is sandwiched between the optical fiber end face and the sensor head.

In an alternate embodiment, free-space optical elements (lenses, mirrors, beam-splitters, filters and similar components) direct light from a light source to the sensor, collect light reflected by the sensor and direct reflected light to the light detector.

In a further embodiment, integrated optical elements (waveguide, coupler, Mach-Zehnder) direct light from a light source to the sensor and collect light reflected by the sensor, and direct reflected light to the light detector.

In a still further embodiment, the sensor is mounted adjacent to a laser diode. Light emitted by the laser diode is incident on the sensor and some of the light reflected by the sensor returns to the laser diode. The monitor photodiode included in the laser-diode housing is used to monitor the light reflected by the sensor.

For detecting multiple analytes the sensor apparatus can include of an array of discrete analyte-binding regions, each region can be effective to bind a different analyte. In one embodiment, the optical fiber includes a plurality of individual fibers each aligned with one of the analyte-binding regions, and the detector includes a plurality of detection areas the optical coupling functions to couple the detection areas with the optical fibers.

In another aspect, the invention includes a method for detecting the presence or amount of an analyte in a sample. The method involves exposing the sensor head to the sample. Allowing the analyte in the sample to react and bind with the analyte binding molecules immobilized on the second surface. Analyte binding is measured by detecting a change in the amplitude and phase of the motion of the second surface in response to an applied driving signal. The motion is detected by monitoring the optical interference between the reflected light beams from the first and second surfaces to produce a sensor signal.

In one method of detection, the driving frequency is adjusted to be near a resonance frequency of the sensor, and the sensor oscillation amplitude is measured. Analyte binding to the sensor changes the total oscillating mass and thus also changes the sensor resonance frequency. For operation in fluid, all the oscillating mass including trapped and bound water will be measured.

In another method of detection, the driving frequency is adjusted to be near a resonance frequency of the sensor, and the phase of the sensor oscillation relative to the driving signal is measured at nearly constant amplitude. Analyte binding to the sensor results in a phase shift that can be monitored with high sensitivity.

In another method of detection, the driving frequency is adjusted to be near a resonance frequency of the sensor and the dissipation is measured by periodically turning off (pulsing) the driving signal and monitoring the decay of the sensor oscillation. Binding to the sensor surface damps the oscillation and changes the dissipation, D, defined as the sum of all energy losses in the system per oscillation cycle. It is also defined as $1/Q$, i.e. the energy dissipated per oscillation, divided by the total energy stored in system. Rigid structures tend to give low dissipation, while soft structures give higher dissipation especially if there is a lot of coupled water.

In another method of detection, the driving frequency is adjusted to be near multiple resonance frequencies (harmonics, overtones) of the sensor. If the sample is rigidly coupled to the sensor surface, the dissipation is low, and each of the resonance frequencies will show similar response. If the sample is soft and does not fully couple to the sensor oscillation, the dissipation is higher, and each of the resonance frequencies may show a different response.

The detecting step can include directing light from an optical fiber onto the two reflecting surfaces and directing reflected light from the two surfaces onto a light detector via an optical coupling. The detector can be a photodiode where detecting includes monitoring changes in light intensity due to optical interferences between the two reflected light beams.

Where the method is used for measuring the rate of association of analyte to the second surface, the sensor signal can be continuously monitored as analyte binding occurs, until a maximum is reached.

Where the method is used for measuring the rate of dissociation of analyte from the second surface, the reacting steps can include exposing the second surface in a dissociation environment and continuously monitoring changes in the sensor signal until a minimum is reached.

Where the method is used for measuring the amount of analyte present in the sample, the detection is carried out continuously over a period of time sufficient to measure changes in the sensor signal at a plurality of time points.

Where the method is used to measure one or more of a plurality of analytes in a sample, the sensor head is composed of an array of discrete analyte-binding regions, each region being effective to bind a different analyte. The detection step includes monitoring the change in motion of each region of the second surface resulting from binding of analyte to the analyte-binding molecules.

Objects of the present invention include:
To provide a sensor that operates with speed and simplicity.
To provide a sensor that significantly improves sensitivity and accuracy.
To provide a sensor that can operate frequencies well above DC.
To provide a sensor that can monitor both amplitude and phase.
To provide a sensor that can operate without the use of labels for real-time and direct detection of binding.
To provide a sensor that can be made very small.
To provide a sensor capable of measuring a small sample volume.
To provide a low-cost disposable sensor head format.
To provide a sensor that easily scales to a multiplexed array-sensing format for measuring multiple analytes simultaneously.
To provide a sensor suitable for operation in a vacuum, gaseous, or liquid environment.

DETAILED DESCRIPTION

Figure 1A:
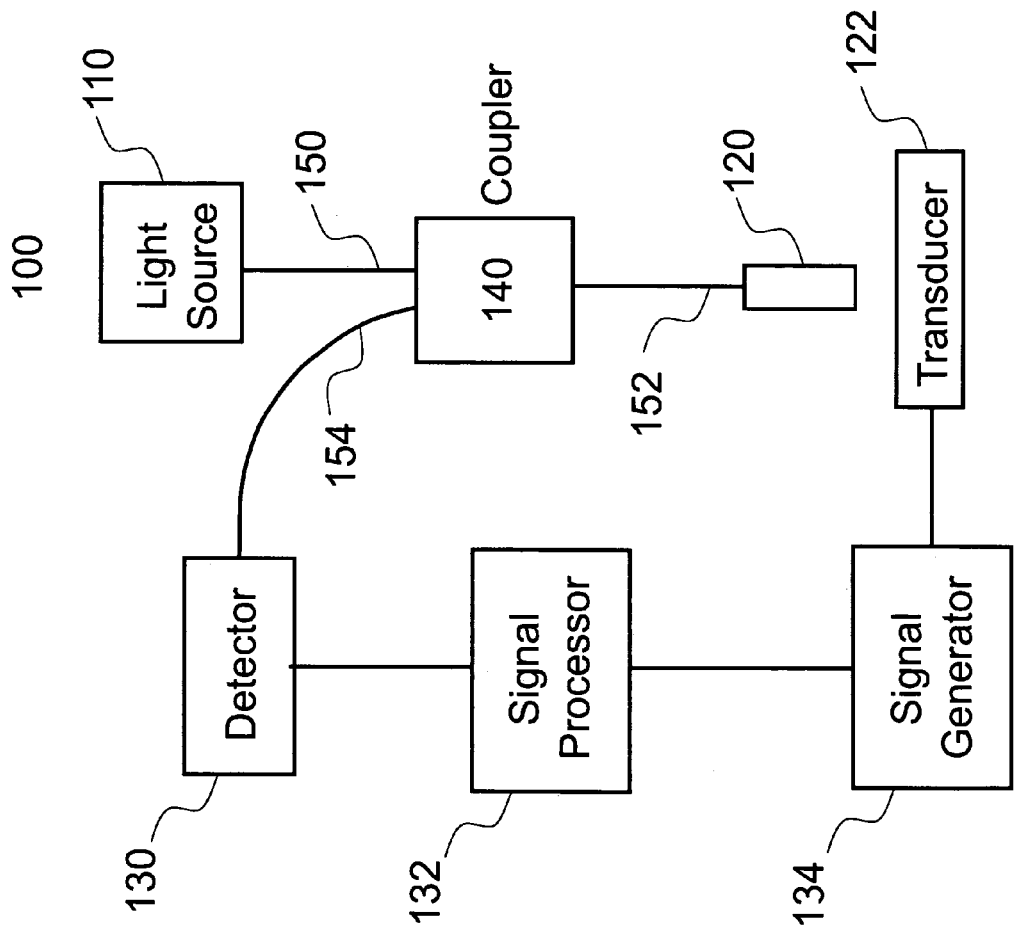
FIG. 1. is a schematic diagram an embodiment of the apparatus using optical fibers.

FIG. 1A is a schematic of the sensor apparatus 100 according to the invention and includes a light source 110, sensor head 120, light detector 130 for detecting optical interference signals from the light waves reflected by the sensor head. An optical coupling 140 assembly directs light to the sensor head and back to the light detector. In one embodiment, the light source, coupler, sensor head and light detector are connected using optical fiber 150, 152, 154. In another embodiment, the light source, coupler, sensor head and light detector are connected using integrated optical waveguides.

In the preferred embodiment, the optical coupling assembly 140 includes a first optical waveguide or fiber 150, 152 connecting the light source to the sensor head and a second optical waveguide or fiber 154 connecting the sensor head to the light detector. An optical coupler, well known in the art, optically couples the first and second waveguides or fibers. The light source 110, optical coupler 140, and light detector 130 components are all commercially available. Signal processor 132 generates a driving signal that is directed to transducer 122. In one embodiment transducer 122 is a solenoid coil that can generate deflections of sensor head components that include magnetic material. In another embodiment transducer 122 is a piezoelectric element capable of producing acoustic or ultrasonic waves in a sample.

Figure 1B:
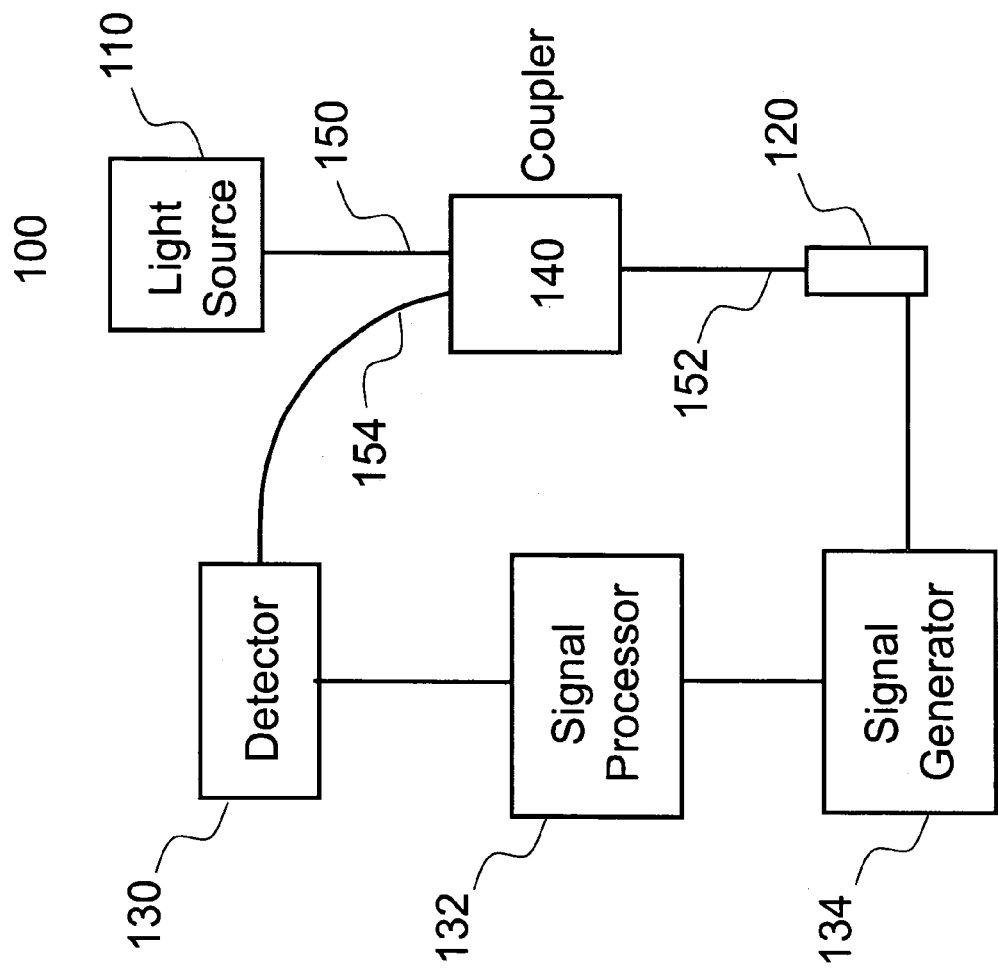

In another embodiment, shown in FIG. 1B transducer 122 is integrated into the sensor head 120 and sensor head components may be driven directly by use of actuating elements on or near the sensor head similar to those described above and including: a piezo-electric devices (for example PZT, PVDF, quartz), magnetically driven elements, electrically driven elements (using electrostatic forces or an electric current), thermally driven elements (for example, a resistive heating element), optically driven elements. Electrostatic forces can deflect the second surface in response to an applied voltage when electrodes are included on or near the two sensor surfaces. In addition, the spacer layer sandwiched by the first and second surfaces may be formed from a piezoelectric material with suitable electrodes.

Figure 2:
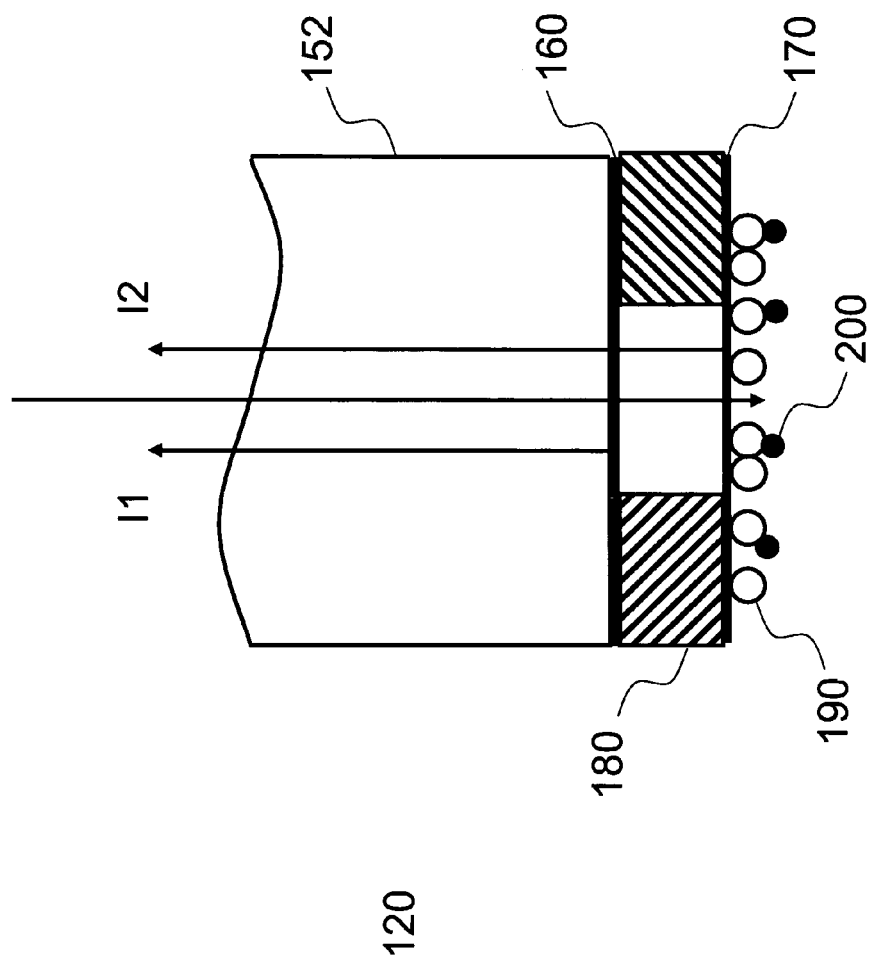
FIG. 2. shows one embodiment of the sensor head
FIG. 3. illustrates the optical interference signal.

FIG. 2 shows a sensor head assembly 120 according to one embodiment of the invention. The sensor head assembly includes: a first surface 160 that is capable of reflecting light, a second surface 170 that is capable of reflecting light and a gap 180 separating the first and second surfaces. The first and second surfaces 160, 170 may have thickness in the range 0.1 nanometer (10-10 meter) to 1 centimeter (10-2 meter). In a preferred embodiment the second surface 170 is a membrane or diaphragm with diameter in the range 10 nanometers (10-8 meters) to 10 centimeters (10-1 meters). The gap 180 may be an air gap and the gap height is preferably set according to the wavelength of the light source to be N lambda/4, where N is an integer, for the maximum sensitivity to deflections of the second surface 170.

Analyte-binding molecules 190 may be immobilized on the second surface 170 such that, when the sensor head 120 is exposed to the sample, analyte molecules 200 specifically bind to the second surface 170 with high affinity. A specific binding reaction is by definition a saturable reaction, usually reversible, that can be competed by an excess of one of the reactants. Specific binding reactions are characterized by a complementarity of shape, charge and other binding determinants as between the participants in the specific binding reaction. The analyte and anti-analyte molecules may be members of a binding pair, examples include: antibodies, DNA, RNA, protein, small and large molecules, cells, receptors and their binding targets, toxins.

The first surface 160 may be simply the bare end-face of an optical fiber. In this case the reflectivity is determined by the refractive index of the glass forming the fiber and the air or fluid forming the gap. Alternately the first surface 160 may include a single or multilayer coating to control the optical reflectivity. For example, a layer of a higher refractive index material (for example, Ta2O5) or a multilayer dielectric thin film stack (alternating SiO2 and Ta2O5 as is well known in the art) may be designed to produce the desired reflectivity. Further, the first surface 160 may include a thin metal film (for example, gold) with the thickness of the film selected to produce the desired reflectivity. The first surface 160 functions to reflect a portion of the light arriving from the light source 110 and is preferably mounted on a rigid substrate.

The second surface 170 may also include a single layer or multilayer thin film stack, for example a dielectric such as SiO2, Ta2O5, a polymer layer or layers, or a metal thin film or metal foil, similar to the first surface 160. The second surface 170 may also be partially or fully reflective in order to reflect some or all of the light arriving from the light source 110. The second surface 170 is supported near the first surface 160 by a spacer layer 180 that forms the gap but it is otherwise free to move in response to an applied force or pressure. The gap distance is in the range 1 nm (10-9 meters)-1 cm (10-2 meters) and selected according to the wavelength of illumination in order to optimize sensitivity. The thickness of the second surface 170 may be selected according to the desired sensitivity, with sensitivity increasing as the thickness decreases. In a preferred embodiment the second surface 170 is supported by the spacer layer 180 to form a membrane or diaphragm. The membrane or diaphragm may be held in tension to control the resonance frequency and optimize sensitivity. In the case of a liquid sample, the membrane may be exposed to the sample on only one side. One the second side there is a gap, preferably and air-gap, formed by the spacer layer 180 and the first surface 160.

In addition, the first surface, spacer layer, and second surface may include polymer materials. For example, the spacer layer may be formed from a piezo-electric film (for example, PVDF, PZT, quartz). In addition, the first surface may include a polymer layer to provide a flexible substrate for the spacer layer and second surface.

In addition to the membrane or diaphragm there are a variety of alternate configurations for the second surface. For example the second surface may be formed by:

a ribbon: a reflecting surface supported at two ends.

a trampoline: a reflecting surface supported by three or more arms.

a porous element: for example a membrane, ribbon, trampoline having an array of holes.

In the preferred embodiment, as analyte molecules 200 bind to their binding partners 190 on the second surface 170, the added material changes the response of the second surface 170 to an applied force or pressure. In the special case where the second surface forms a membrane with the following parameters:

| radius | r | (meters) |
|---|---|---|
| surface mass density | Ma | (kg/m^2) |
| membrane surface tension | T | (N/m) |
| transverse wave velocity | Vt | (m/s) |

Then Vt=SQRT(T/Ma) and the lowest resonance frequency is:

$$\omega res = 2.40483\ Vt/r\ (Hz) = 2.40483/r\ SQRT\ (T/Ma)\ (Hz)$$

where the numerical factor 2.40483 is the first root of the zero-th order Bessel function J0(x) and the entire membrane oscillates up and own in this lowest order standing wave.

As an example, if we first consider a gold membrane in air with radius 5 um, thickness 0.1 um.

The surface mass density determined from the volume density and thickness:

$$\text{Mass density } 19320\ kg/m^3 \times 0.1\ um = 1.932 \times 10^{-3}\ kg/m^2$$

Membrane surface tension is ~0.1 N/m

Then the fundamental resonance frequency fres ~550 KHz.

If the noise floor is approximately 0.01 Hz then the smallest detectable change in mass density is given by the relation:

$$\Delta Ma/Ma = 2\ \Delta fres/fres,$$

and the smallest detectable change in mass density is approximately 10 picogram/cm^2=10-11 g/cm^2. This is just one example and even higher sensitivities may be achieved by further optimization of the sensor parameters. It is also possible to operate the sensor at higher harmonic or overtone frequencies to obtain additional information about analyte binding. This analysis is for the case of a membrane in air and does not take into account the effects of a liquid.

Generally, the presence of a liquid will introduce viscous damping, tending to lower the resonance frequency.

On the typical length scales of the sensor apparatus working with a liquid sample, viscous forces dominate inertial forces. That is, in the preferred embodiment, the Reynolds number is low and fluid flows will be laminar (and usually not turbulent).

Conventional immobilization chemistries may be used to attach the analyte-binding layer 190 to the second surface 170. The analyte-binding layer 190 can be either a monolayer or a multilayer matrix. A siloxane technique is available for attachment to glass surfaces and a variety of techniques are available for attachment to gold surfaces.

Figure 3:
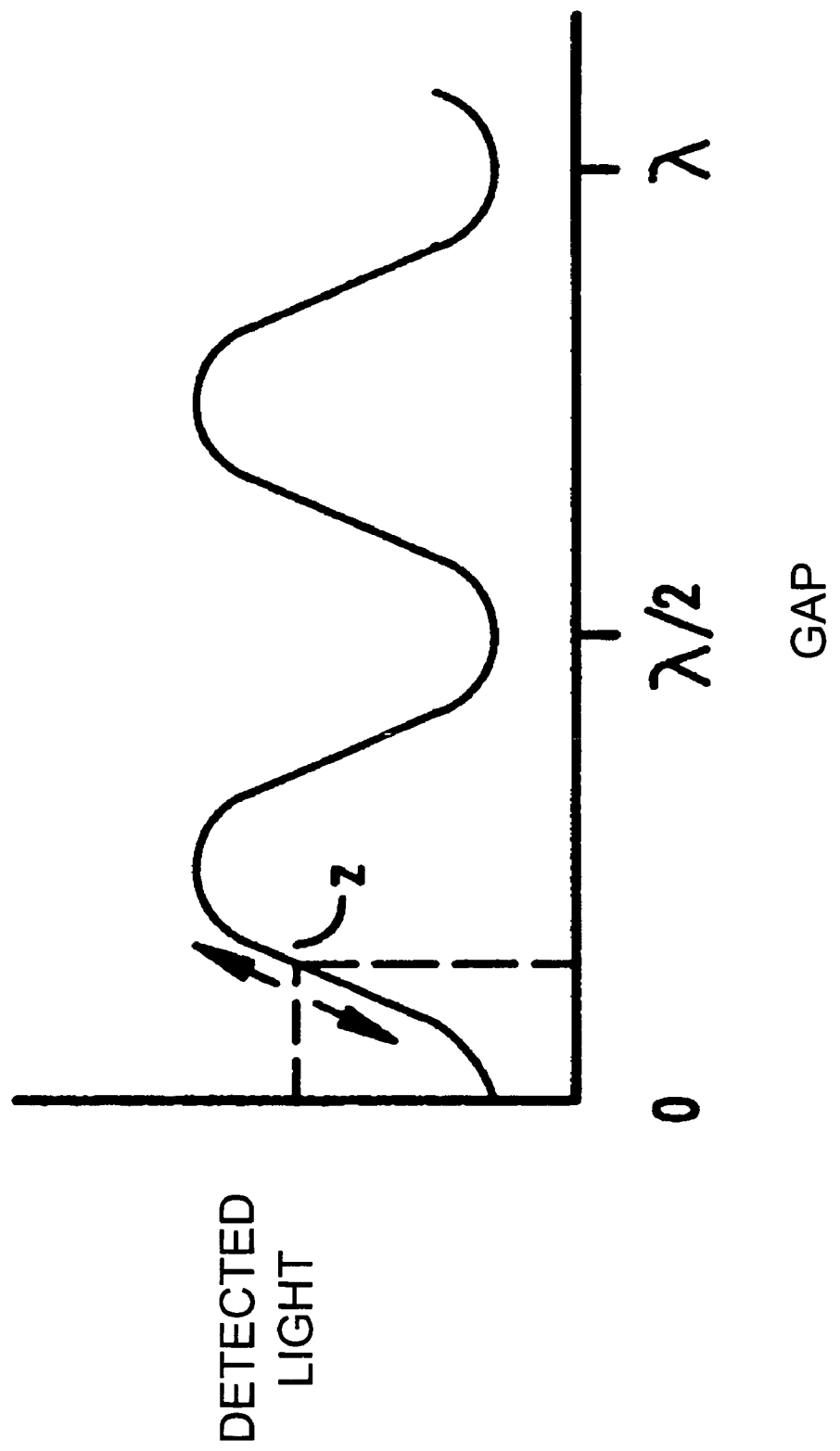

As shown in FIG. 3, the measurement of the presence, concentration and/or binding rate of analyte to the sensor head 120 is enabled by the optical interference of the light waves reflected by the two surfaces 160 and 170 in the sensor head. The operation of the sensor in the preferred embodiment may be understood by assuming that there are two reflected light waves from the first and second surfaces 160, 170. The first surface 160 generates a reflected wave with electric field E1, where the electric field is a vector having both amplitude and direction, in this case we are primarily concerned with the amplitude and phase.

The second surface 170 generates a reflected wave with electric field E2. The interference of the two reflected light waves generates a new wave with electric field:

$$E = E1 + E2.$$

The light detector 130 measures the light intensity given by:

$$I\text{detector} = |E\text{detector}|^2 \sim |E1+E2|^2 = I1 + I2 + 2 * I1 * I2 * \cos(2*pi*DELTA/Lambda)$$

Where DELTA is the optical path difference between the two surfaces 160, 170 and lambda is the wavelength of the light from the light source. The gap between the two surfaces is GAP=DELTA/2n, where n is the refractive index of the material filling the gap. In general, the electric fields E1 and E2 will have different amplitudes, but in the special case where the amplitudes are the same |E1|=|E2|=|E| the analysis is easier.

In this case, the maximum light intensity is:

$$I\max \sim |2E|^2 = 4I,$$

This maximum light intensity occurs when the optical path difference is:

$$DELTA = N\ Lambda,\ \text{where N is an integer.}$$

Also in this case, the minimum light intensity is:

$$I\min = |E-E|^2 = 0$$

This minimum light intensity occurs when the optical path difference is:

$$DELTA = N\ Lambda/2.$$

and when the optical path difference DELTA=(2N+1) Lambda/4, the light intensity is:

$$I\text{quadrature} \sim 2I$$

At this intensity, called the quadrature point, the light intensity is in the middle of its range.

For example, in the special case where N=1 and air fills the gap (n=1.0) and the wavelength Lambda=1000 nanometers (10-6 meters)

Imax occurs when GAP=500 nm

Iquadrature occurs when GAP=375 nm

Imin occurs when GAP=250 nm

So the detected light intensity varies from minimum to maximum as the gap between the two reflecting surfaces varies by a distance equal to ¼ of the wavelength of the light source or, in this case, 250 nm.

As described in more detail below, mechanical motion, deflection or oscillation of the second surface 170 may be driven by a variety of forces including: viscous, elastic, acoustic, ultrasonic, inertial, thermal, electrostatic, magnetic, piezo-electric and others.

In one embodiment, the second surface 170 is exposed to an applied force or pressure generated by an external source. For example, a piezo-electric element may be mounted in such a way that it is exposed to the sample and driven by a driving signal to generate acoustic or ultrasonic pressure waves in the sample, as is well known in the prior art.

In another embodiment, the first or second surfaces 160, 170 may include a layer of magnetic material. An externally controlled magnetic field, for example a solenoid coil, may be used to apply a force to the magnetic layer, thus displacing the first surface relative to the second surface.

In one implementation, as described by Lindsay in U.S. Pat. No. 5,513,518, a thin film or particles of magnetic material 172 is applied to the second surface 170 with the direction of the magnetic moment M along the perpendicular to the plane of the surface. A small solenoid 122 is placed near second surface 170 so as to generate a magnetic field B that is predominantly perpendicular to the magnetic moment of the magnetic film. Construction of a suitable solenoid and choices of magnetic materials is known to those of ordinary skill in the art. For the purpose of modulating the deflection of the second surface 170, a signal voltage source 134 is used to drive the solenoid 122. The second surface deflection is detected by optical detector 130 and delivered to a synchronous signal processor 132 which receives the signal voltage 134 as a reference. The synchronous detector is used to monitor both the amplitude and phase of the second surface deflection, an adjustable time constant for integration of the signal may be used to improve the signal to noise ratio.

An important step in the preparation of second surface 170 is the formation of a controlled magnetic moment. One method for doing this is to place the surface in a strong magnetizing field. In another method, a thin film of Cobalt is evaporated onto the surface; such a film is relatively easy to magnetize in the plane of the film.

In an alternate embodiment the sensor is driven directly by use conductive elements, or electrodes, on or near the first and second surfaces so that a voltage applied to the electrodes generates an attractive force, by capacitive coupling, tending to pull the first and second surfaces together as is well known in the prior art.

In a further embodiment, the first or second surfaces 160, 170, the spacer layer 180 or one or more the mounting elements shown in the figures, may include a piezo-electric element having suitable electrodes. A driving signal voltage applied to these electrodes generates a change in the shape or size of the piezo-electric element generating a pressure wave and displacing the first surface relative to the second surface.

Still further, the first or second surfaces 160, 170 may include a resistive layer having suitable electrodes. A driving signal voltage applied to these electrodes causes resistive heating and leads to a change in shape or size of the resistive layer or adjacent layers, thus displacing the first surface relative to the second surface.

Still further, the first or second surfaces 160, 170 may include electrodes suitable to carry electric current. An ambient magnetic field (for example, the earths magnetic field) or an externally controlled magnetic field, for example a solenoid coil, may be used to apply a force to the current-carrying electrodes, thus displacing the first surface relative to the second surface.

Still further, the first or second surfaces 160, 170 may include one or more layers of material that change shape or size in response to temperature changes. It is then possible to displace the first surface relative to the second surface by controlling the temperature of the sample near the sensor head. For example, if the second surface includes two layers of dissimilar metals, a temperature change of the sample near the sensor head will cause a displacement of the second surface relative to the first surface due to the well known bi-metallic effect.

In one method of operation, the sensor head 120 is exposed to a sample that includes an analyte and the sensor head 120 is also exposed to a drive signal from signal generator 134, of fixed frequency and fixed amplitude. The frequency and amplitude of the pressure wave are selected to optimize the response of the sensor head 120. The second surface 170 moves in response to the applied drive signal and this movement is detected as a change in the optical interference signal at the light detector. Analyte binding to the second surface changes the response of the second surface 170 to the applied drive signal, for example by changing the fundamental resonant frequency of the second surface 170 to produce a change in the amplitude of the second surface response.

In another method of operation, the sensor head 120 is exposed to a sample that includes an analyte and the sensor head 120 exposed to a driving signal of known frequency, amplitude and phase. The frequency, amplitude and phase of the driving signal are selected to optimize the response of the sensor head 120, and may be fixed or variable. The second surface 170 moves in response to the applied driving signal and this movement is detected as a change in the optical interference signal at the light detector. Analyte binding to the second surface changes the response of the second surface 170 to the applied driving signal and the phase of this response can be compared to the phase of the driving wave while the frequency and amplitude of the response are nearly constant.

In an alternate method, the sensor head 120 is exposed to a sample that includes an analyte and is also exposed to a drive signal of fixed amplitude but variable frequency. The frequency can be swept over a range anywhere from 1 Hz to 1 GHz, the frequency can be set at a number of discrete frequencies or the frequency can be swept continuously over a defined frequency range and then jump to another defined frequency range, according to the optimum response of the sensor head 120. The second surface 170 moves in response to the applied drive signal and this movement is detected as a change in the optical interference signal at the light detector. The measured amplitude of the motion of the second surface in response to the swept-frequency pressure wave is used to generate an amplitude response spectrum. Analyte binding to the second surface 170 changes the measured amplitude response spectrum, for example by changing the fundamental resonant frequency and also changing the harmonics or overtones.

In an alternate method, the sensor head 120 is exposed to a sample that includes an analyte and is also exposed to a pressure wave of variable amplitude and variable frequency. The frequency can be swept over a range anywhere from 1 Hz to 1 GHz, the frequency can be set at a number of discrete frequencies or the frequency can be swept continuously over a defined frequency range and then jump to another defined frequency range, and the amplitude can be according to the optimum response of the sensor head 120. The second surface 170 moves in response to the applied drive signal and this movement is detected as a change in the optical interference signal at the light detector. The measured amplitude of the motion of the second surface in response to the swept-frequency drive signal is used to generate an amplitude response spectrum that can be normalized to the known driving amplitude. Analyte binding to the second surface 170 changes the measured amplitude response spectrum, for example by changing the fundamental resonant frequency and also changing the harmonics or overtones.

In a further method, the sensor head 120 is exposed a sample that includes an analyte and is also exposed to a driving pulse or step-function with a defined rise-time, fall-time, amplitude, duty ratio and cycle time (repetition rate). These parameters are selected according to the optimum response of the sensor head. The amplitude and frequency of motion of the second surface 170 in response to the driving pulses may be measured at the fundamental frequency and at the harmonics or overtones. Analyte binding to the second surface changes the measured response.

When the driving force is abruptly turned off, the second surface oscillation amplitude decays with time. By monitoring the decay of the second surface oscillation it is possible to measure the dissipation, D. The speed with which the oscillation amplitude decays is inversely proportional to the dissipation D, defined as:

$$D = 1/Q = (\text{energy dissipated per cycle})/(2pi \text{ total energy stored})$$

The dissipation factor may be measured every time the driving wave generator output is stopped and the sensor oscillation starts to decay exponentially. A soft film attached to the sensor is deformed during the oscillation, which gives a high dissipation while as a rigid material gives a low dissipation.

Measuring both the changes in the resonant frequency and the dissipation factor can provide additional information about the sample. Further, measuring changes in the resonant frequency and the dissipation factor for multiple oscillating modes of the sensor can provide still more information about the sample.

In a still further method, the sensor head 120 is exposed to a sample including an analyte and the design of the sensor head is optimized to detect changes in surface stress, for example, by selecting the second surface dimensions and geometry as well as by selecting the material and layer thicknesses of a single or multilayer structure.

Analyte binding to the second surface 170 changes the surface stress and causes a change in position, or displacement of the second surface relative to the first surface. The displacement of the second surface can be continuously monitored.

In a still further method, the sensor head 120 is exposed to a sample including fluid flow with a defined flow velocity. The speed and direction of the flow are selected according to the optimum response of the sensor head. The motion of the second surface 170 in response to the fluid flow is measured. Analyte binding to the second surface changes the measured response due to changes in effective mass, surface stress, viscosity, elasticity and other effects.

Further, molecules and particles in the sample may impact or collide with the sensor head 120 as they are carried by the fluid flow. The response of the second surface 170 to the impact of the molecules and particles can also be measured.

In a still further method the sensor head 120 is exposed to a sample including motile components, for example sperm or bacteria. The design of the sensor head 120 is optimized to detect the motile components. The transient impact of one or more motile components with the second surface may cause a detectable deflection of the second surface 170. In addition, when the second surface 170 is coated with an analyte-binding layer specific to the desired motile component, the motion of the second surface 170 can be continuously monitored when one or more of the motile components binds and continues to move while attached to the sensor surface.

Figure 4:
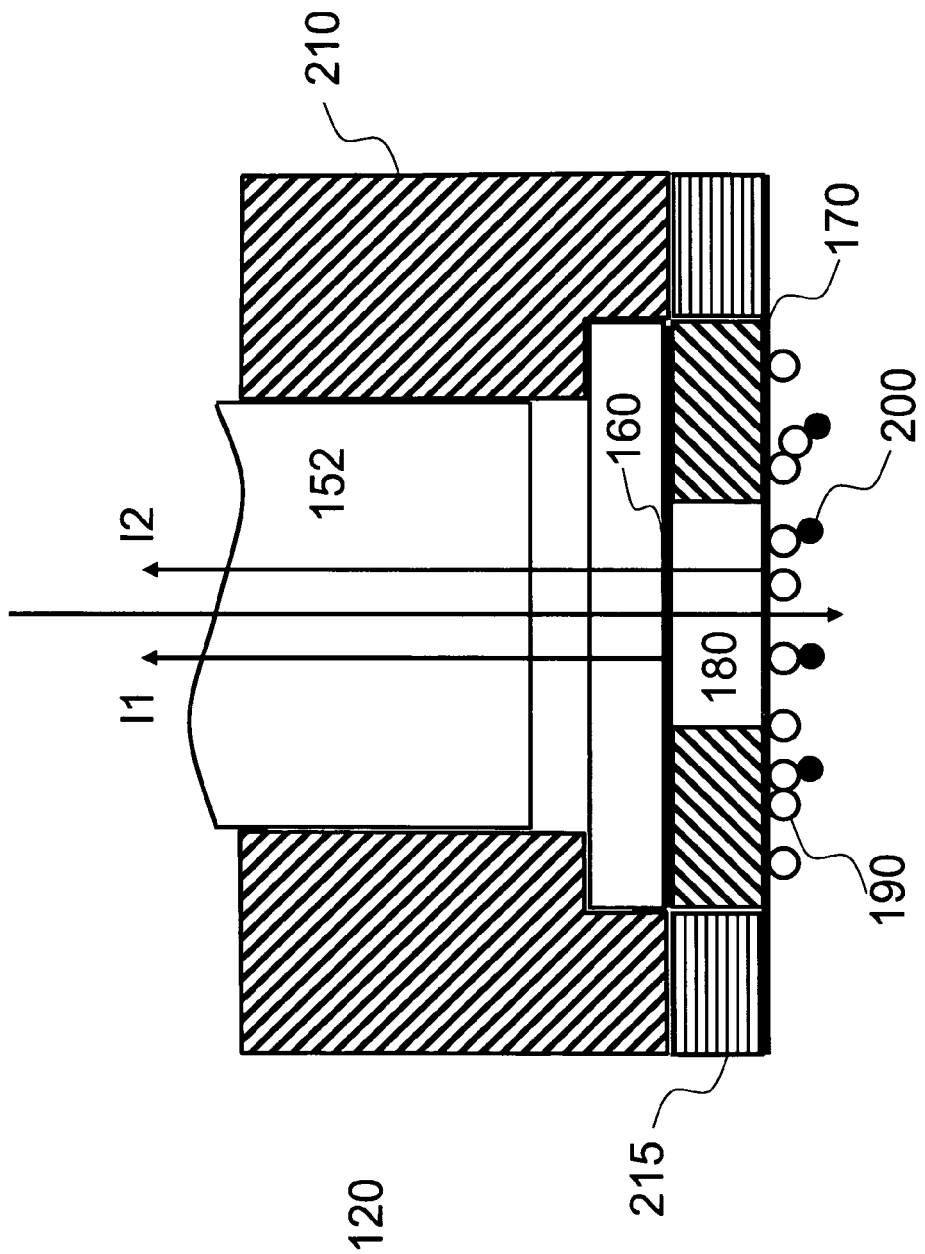
FIG. 4. is a schematic of another embodiment of the sensor head.

FIG. 4 shows an embodiment of the invention including a sensor head 120 that is removably carried on an optical fiber in the assay apparatus. The sensor head assembly 120 includes a first surface 160 that is capable of reflecting light and is mechanically fixed, a second surface 170 that is capable of reflecting light and a gap 180 separating the first and second surfaces 160, 170 that is typically an air gap, but may be a fluid-filled gap or a vacuum. The gap height is preferably set according to the wavelength of the light source as described previously for maximum sensitivity to deflections of the second surface 170. In a preferred embodiment the second surface 170 is a thin membrane or diaphragm held in tension by a tensioning element 215. Alternately, the spacer layer 180 attached to the second surface 170, or the first surface 160 may serve as a tensioning element. Analyte-binding molecules 190 may be immobilized on the second surface 170 such that, when the sensor head 120 is exposed to the sample, analyte molecules 200 specifically bind to the second surface 170 with high affinity. In this embodiment, the entire sensor head 120 may be removably attached to an optical fiber 152 by use of a mating ferrule and cylinder, as is well known in the art of fiber optic connectors.

In one embodiment the second surface 170 is also removable and can be easily replaced. This allows for a low-cost disposable second surface 170 so that a new and fresh surface can be used for each sample test. In another embodiment, the second surface 170 or the entire sensor head 120 can be removed and discarded after use to provide a fresh second surface is used for each measurement. In another embodiment, the second surface 170 can be cleaned by sonication, or ultrasonic cleaning, in a suitable cleaning solution after use. The sonication process may occur in the same assay apparatus used to make measurements simply by replacing the measurement buffer with a cleaning solution and using a transducer operating at appropriate amplitude and frequency to generate the sonication cleaning energy. Alternately, the sonication process may occur in a separate chamber specifically optimized for sensor cleaning. If necessary, a fresh layer of analyte-binding molecules can then be attached to the cleaned surface. In this case the sensor head is reusable for multiple measurements.

In a further embodiment, first and second surfaces 160, 170 can be integrated into a sensing assembly, separate from the optical fiber 152. In this case, first surface 160, second surface 170 and spacer 180 form a sensor assembly that is removably attached to an optical fiber 152 by use of a mounting element 210. The first surface 160 may include a substrate to form an optical element having a single or multilayer coating that serves as the first reflecting surface. The space between the end face of optical fiber 152 and the first surface 160 may include an air gap. The size of the air gap can be selected to minimize the effect of reflections from the fiber end face. If the air gap is significantly greater than the coherence length of the light source, the effect of optical interference form the light reflected by the fiber end face will be minimal. In another embodiment the end surface of optical fiber 152 may be modified to minimize reflected light, for example by use of a multilayer anti-reflection coating, or by angle-polishing the end surface, by use of an index-matching fluid or gel, or similar methods. In operation the sensor head 120 is connected to an optical fiber 152 by use of mounting element 210 and seated or locked in place. The sensor head 120, for example, may then be exposed to a sample including analyte under conditions that provide for the binding of sample analyte to the analyte-binding molecules immobilized on the second surface 170 according to the methods of the invention previously discussed.

Figure 5A:
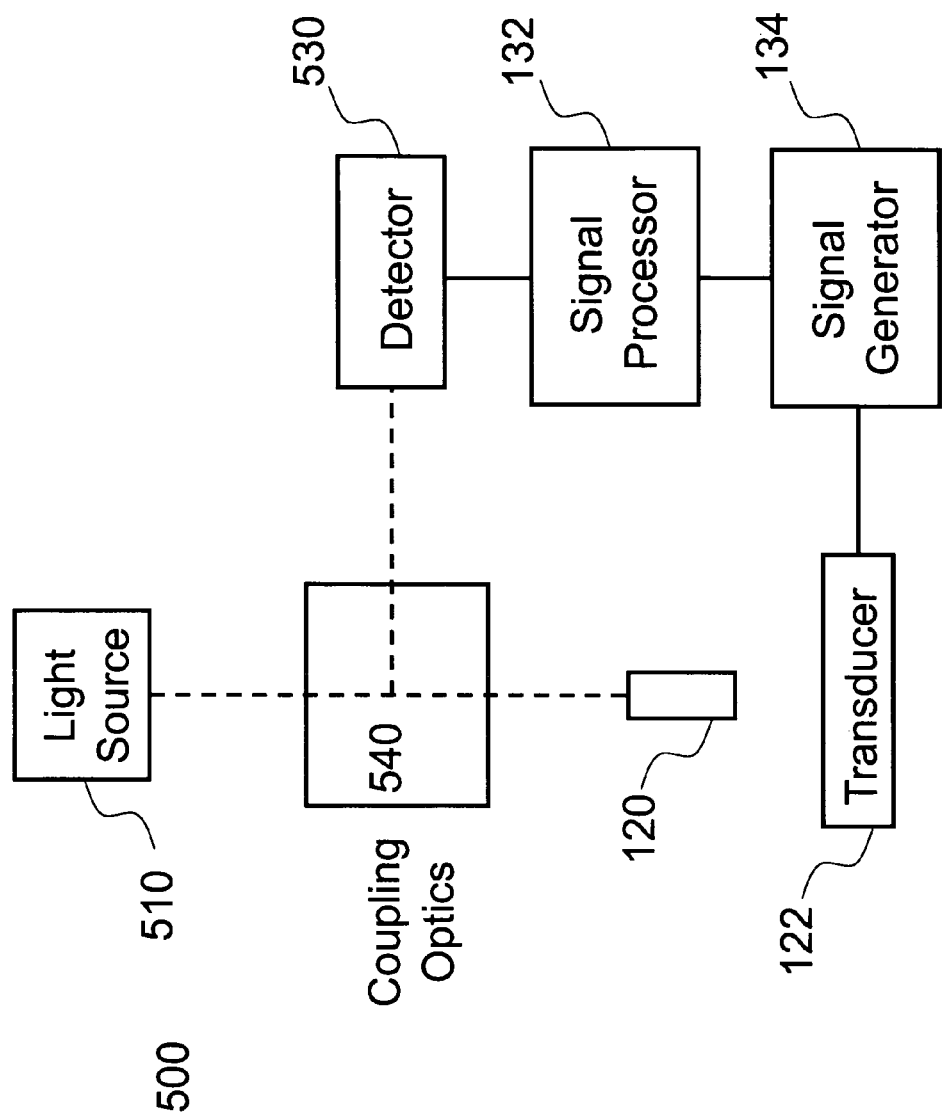
FIG. 5. is a schematic diagram an alternate embodiment of the apparatus using free-space optics.

FIG. 5A shows an alternate embodiment of the sensor apparatus, 500, using free-space optics. In this case, a free-space optical system 540 (which may include a variety of components such as lenses, mirrors, beam-splitters, optical coatings, prisms, gratings, molded optical elements and associated mounting components) is used to direct light from the light source 510 to the sensor head 120 and to collect the reflected light from the sensor head and direct it to the light detector 530. This embodiment may require tight tolerances and precise alignment of the components of the optical system.

The light source 510, may be a LED, laser diode, solid state laser, gas laser, and suitable wavelengths range from the DUV to the far infrared (10 nm to 100 um). The light source 510 may emit light primarily at a single wavelength or over a range of wavelengths. The detector 530 may be a simple single-element photodetector, multi-element photodetector or a detector array, such as a charge-couple device CCD or CMOS imaging device.

A single detector element can be used to monitor the signal from the sensor head 120.

The light source 510, coupling optics 540, and light detector 530 components are all commercially available.

Figure 5B:
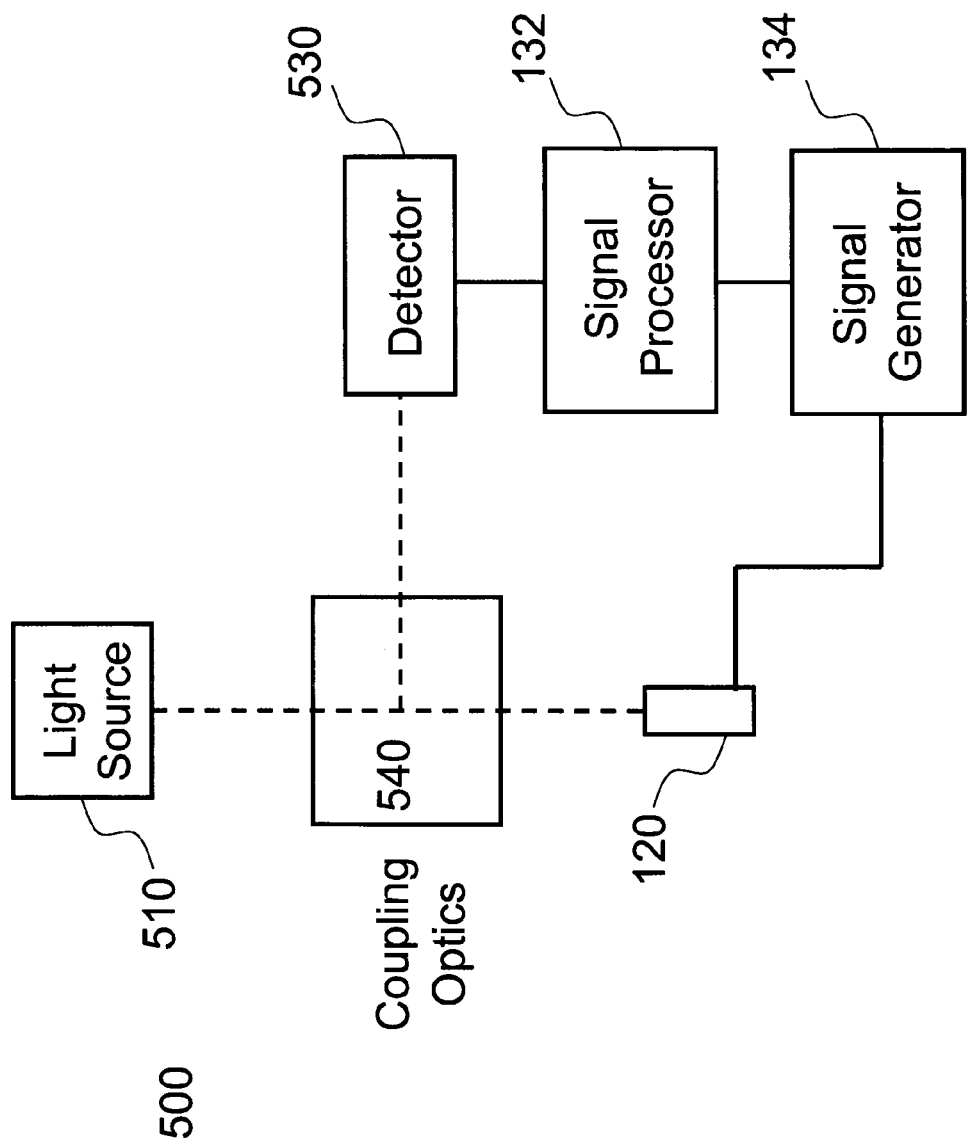

In another embodiment, shown in FIG. 5B transducer 122 is integrated into the sensor head 120 and sensor head similar to the situation previously described in FIG. 1B.

Figure 6:
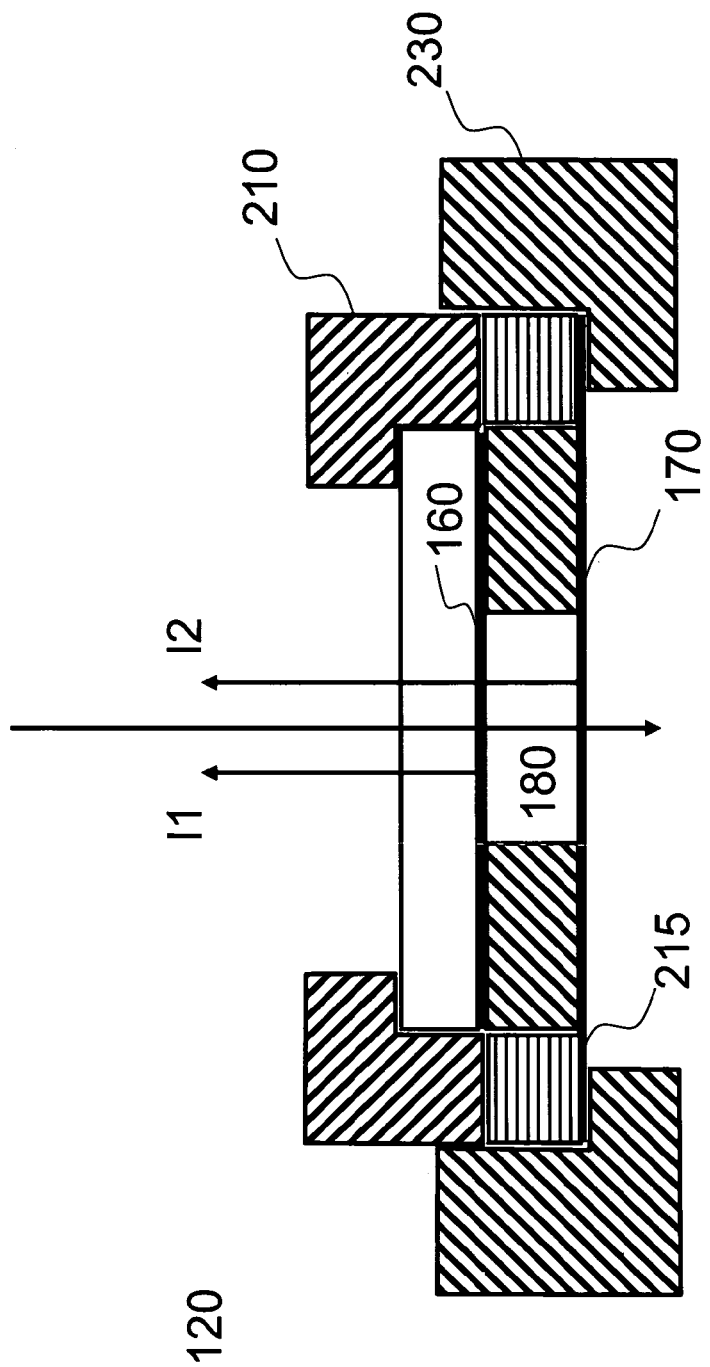
FIG. 6. is a schematic of another embodiment of the sensor head compatible with free-space optical apparatus.

FIG. 6 shows an embodiment of the invention including an embodiment of sensor head 120 designed for a free-space optics-based assay apparatus. The sensor head assembly 120 includes a first surface 160 that is capable of reflecting light and is mechanical fixed, a second surface 170 that is capable of reflecting light and a gap 180 separating the first and second surfaces 160, 170 that is typically an air gap but may be fluid-filled or simply a vacuum. The gap height is preferably set according to the wavelength of the light for the maximum sensitivity to deflections of the second surface 170 as discussed previously. In a preferred embodiment the second surface 170 is a thin membrane or diaphragm held in tension by a tensioning element 215. Alternately, the spacer layer 180 attached to the second surface 170 may serve as the tensioning element. Analyte-binding molecules 190 may be immobilized on the second surface 170 such that, when the sensor head 120 is exposed to the sample, analyte molecules 200 specifically bind to the second surface 170 with high affinity. In this embodiment, the entire sensor head 120 may be removably mounted in a carrier 230 for alignment with the coupling optics 540 of the free-space optics assay apparatus 500.

In one embodiment the second surface 170 is removable and can be easily replaced. This allows for a disposable second surface 170 so that a new and fresh surface can be used for each sample test. In another embodiment, the second surface 170, the second surface and spacer 170, 180, the second surface, spacer and first surface 160, 170, 180 or the entire sensor head 120 can be removed cleaned and re-used or removed and discarded after use. In this way a fresh second surface 170 can be used for each measurement.

In another embodiment, the second surface 170 can be cleaned by sonication, or ultrasonic cleaning, in a suitable cleaning solution after use. The sonication process may occur in the same assay apparatus used to make measurements simply by replacing the measurement buffer with a cleaning solution and using a pressure wave transducer operating at appropriate amplitude and frequency to generate the sonication cleaning energy. Alternately, the sonication process may occur in a separate chamber specifically optimized for sensor cleaning. If necessary, a fresh layer of analyte-binding molecules can then be attached to the cleaned surface. In this case the sensor head is reusable for multiple measurements.

In one embodiment the first surface 160 includes a substrate to form an optical element having a single or multilayer coating that serves as the first reflecting surface.

The space between the coupling optics and the first surface 160 may include an air gap. The size of the air gap can be selected to minimize the effect of undesired reflections from optical elements of the sensing apparatus. If the air gap is significantly greater than the coherence length of the light source, the effect of optical interference form the light reflected by the fiber end face will be minimal. In another embodiment the optical elements of the sensing apparatus may be modified to minimize reflected light, for example by use of a multilayer anti-reflection coating, or by angle-polishing the end surface, by use of an index-matching fluid or gel, or similar methods.

In operation the sensor head 120 is aligned with the free-space optical system 500 by use of mounting element 230 and seated or locked in place. The sensor head 120 can then exposed to a sample of analyte under conditions that provide for the binding of sample analyte to the analyte-binding molecules immobilized on the second surface 170 according to the methods of the invention previously discussed.

Figure 7:
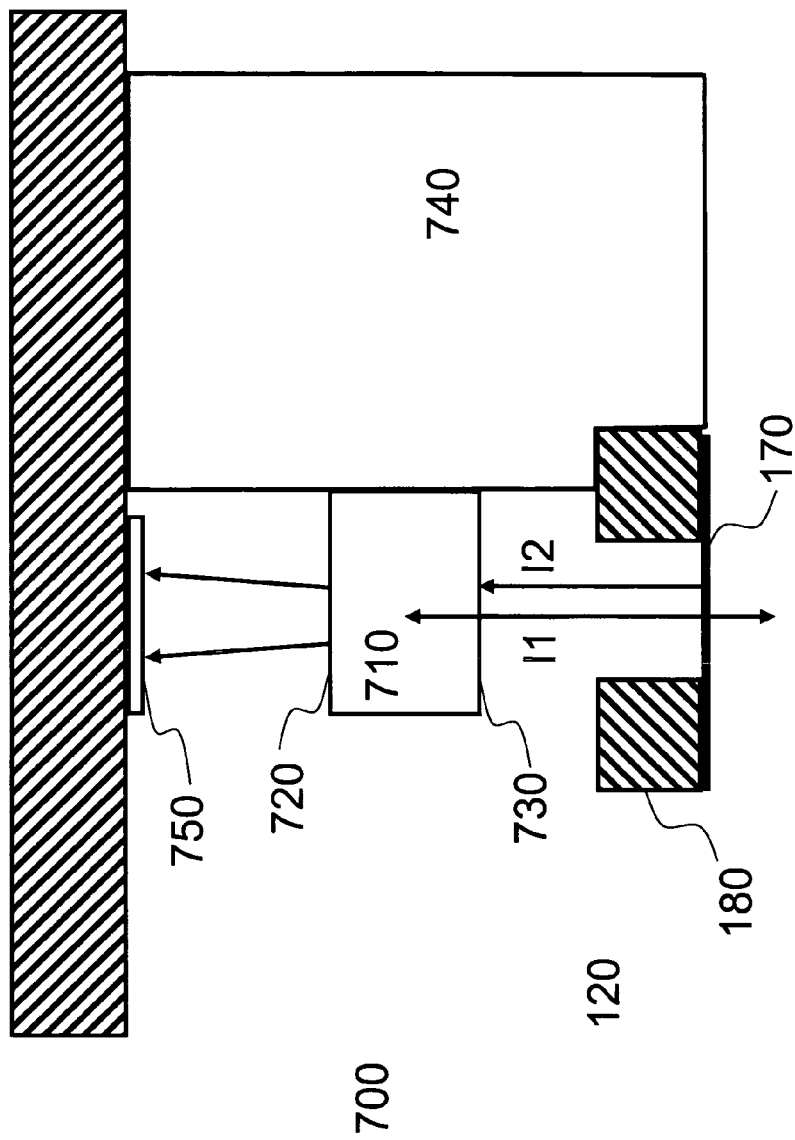
FIG. 7. is a schematic diagram an alternate embodiment of the apparatus using laser diode sensor.

FIG. 7 shows an alternate embodiment of the sensor apparatus 700 using a laser diode sensor. This embodiment includes a laser diode 710 having two light-emitting end-faces 720 and 730. The laser diode 710 is carried by a mount 740 and positioned proximate the sensor 120 with the laser diode light emitting face 730 oriented to direct light to the sensor 120 and receive light from the sensor 120. A light detector 750 is mounted close adjacent the other face of the laser diode 720 for receiving laser light. The light detector 750 generates an electrical signal directly related to the power of the laser light and provides a measure of the displacement of the second surface 170 relative to the first surface 160 of the sensor head 120 by use of optical interference as described previously.

The gap between the first surface 730 and second surface 170 is typically in the range 1 um (10-6 meters) to 1 cm (10-2 meters). Although the light detector 750 is shown separate from the laser diode 710, it is also possible to produce an integrated device combining both light detector 750 and laser diode 710 into a single unit.

A solid state laser comprises a cavity in which light is generated and made to reflect from end to end. Gain is added to the cavity such that the energy of the light continues to increase until the device "lases", i.e. the light energy is sufficient to pass through the reflective surfaces 720, 730 to produce a beam of laser light directed to the second surface of the sensor 170. The light reflected by second surface 170 back into the laser diode 710 adds to the light reflected internally from the front face 730 in a manner which depends on the relative phase. Light reflected by the second surface 170 can add either constructively or destructively with the light in the laser diode cavity and this will vary with the distance between second surface 170 and the laser diode front face 730. Some of the laser diode light output is transmitted by the laser diode surface 720 to the light detector 750 to provide a measure of the laser diode light power output.

The effect of optical interference between light reflected by the two surfaces, 170 and 730 is to produce a variation of the laser diode light power output with gap similar to the variation shown in FIG. 3. When the light reflected by second surface 170 is in-phase with the light reflected by the laser diode front face 730, the laser diode output from face 720 will be a maximum and when the light from the second surface 170 is out-of-phase, the lasers output will be a minimum. If the second surface is moved one-quarter of a wavelength of the laser light, either toward or away from the laser diode front face 730 the output will vary from a maximum to a minimum as depicted in the figure. Using this optical interference effect, displacements of the second surface 170 can be detected by monitoring the changes in the laser output power as sensed by the light detector 750. If the laser wavelength is ~1 micron (10-6 meters) this distance is about 250 nanometers, as previously described. To maximize sensitivity, the modulation of laser diode power due to second surface displacement should be as large as possible. This can be achieved by optimizing the position, alignment and reflectivity of all optical surfaces.

Figure 8:
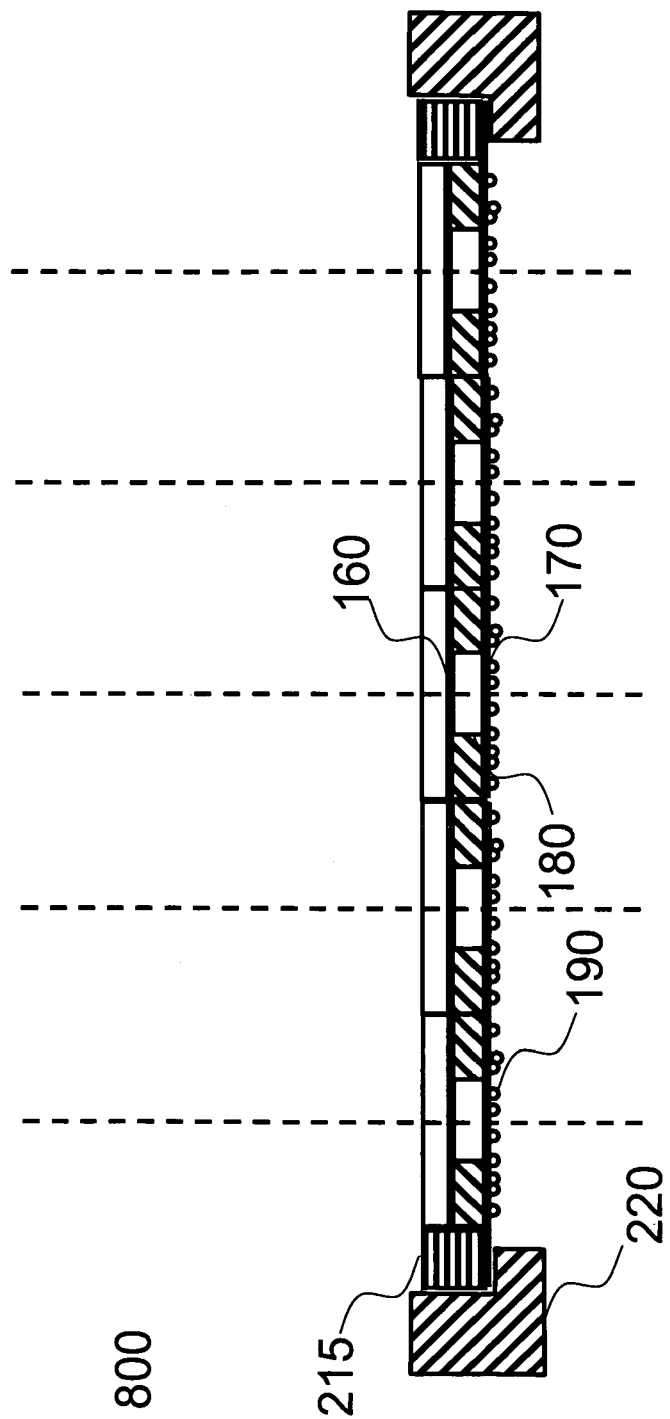
FIG. 8. is a schematic of a multiplexed embodiment of the sensor head suitable for multiple analytes.

FIG. 8 illustrates a sensor assembly in an embodiment of the invention designed for detecting one or more of a plurality of analytes in a sample. In the case of a sensor apparatus using optical fibers, individual optical fibers may be mounted in a carrier, for example a multi-fiber ferrule, to provide for precise alignment of both position and angle for each fiber in the array. The array may be linear (1-dimensional) or aerial (2-dimensional). Alternately the individual fibers may be fused to form a fiber bundle.

The sensor assembly 800 is composed of the same elements described previously for the sensor head in FIG. 4, but in an array format. In one embodiment, an array of first reflecting surfaces 160 may be formed on the fiber end surfaces. Further, an array of second surfaces, 170 each of which is movable in response to an applied force or pressure, is positioned near the first reflecting surfaces and spaced by a gap. A spacer layer 180 having a thickness selected for optimum sensitivity is sandwiched between the first and second surfaces 160, 170 to define a gap. In a preferred embodiment the second surface 170 is a thin membrane or diaphragm held in tension by a tensioning element 215 in a mount 220. Alternately, the spacer layer 180 attached to the second surface 170, or the first surface 160 may serve as a tensioning element. Each of the second surfaces 170 may have an immobilized layer of analyte-binding molecules 190 specific for one or more of the analytes in the sample.

In one embodiment, the array of second surfaces 170 is removably mounted and aligned to the fibers in the fiber array by use of a mechanical mount that mates to the multi-fiber ferrule or fiber bundle. In this way, each of the optical fibers is aligned with an element in the sensor array 800 and each fiber is directing light to and receiving light from one of the elements in the sensor array.

As previously discussed with reference to FIG. 4, a second optical element having a single or multilayer coating can also serve as the first reflecting surface 160. In this case, the space between the end face of optical fiber 152 and the first reflecting surface 160 also includes a gap. The size of the gap 180 can be selected to minimize the effect of reflections from the optical fiber end-face. If the gap 180 is significantly greater than the coherence length of the light source, the effect of optical interference from the light reflected by the optical fiber end face will be minimal. In another embodiment the optical fiber end surfaces may be modified to minimize reflected light, for example by use of a multilayer anti-reflection coating, or by angle-polishing the end surfaces, by use of an index-matching fluid or gel, or similar methods.

In addition, the optical coupler in the apparatus which serves to couple the fibers in the array to both the light source and light detector directs reflected light from each element in the sensor array to a corresponding area on a detector array, for example a two-dimensional CCD, a CMOS detector array or a PIN photodiode array. In this way, the signal from each element in the sensor array can be monitored by a corresponding element in the light detector array.

In an alternate embodiment, the sensor apparatus 800 may include free-space optics. In this case, the sensor apparatus includes a free-space optical system similar to the one described previously in FIG. 5. The free-space optics sensor apparatus is used to direct light from one or more light sources to the sensor elements and to collect the reflected light from the sensor elements and direct it to one or more light detectors. This embodiment may require tight tolerances and precise alignment of the components of the optical system.

The light source or sources may be an LED, laser diode, solid state laser, gas laser, and suitable wavelengths range from the DUV to the far infrared (10 nm to 100 um). The light source or sources may emit light primarily at a single wavelength or over a range of wavelengths. The light detectors may be a simple single-element photodetector, multi-element photodetector or a detector array, such as a charge-couple device CCD or CMOS imaging device. The light source, coupling optics, and light detector components are all commercially available.

The embodiment of the invention using a laser diode sensor previously described in FIG. 7 can also be extended for the detection of one or more of a plurality of analytes in a sample by use of multiple laser diodes, each having a separate mount, or sharing a common mount. Further, it is also possible to use a laser diode bar including multiple laser diode elements.

In one application the sensor array 800 forms a "gene chip" for detecting a plurality of different gene sequences. Each sensing element in the array has an immobilized DNA sequence designed to specifically hybridize with a complementary DNA sequence in the sample. More generally, applications of the apparatus of this invention include:

1. Screening hybridoma expression lines.
2. Characterizing antibody affinity to an antigen.
3. Characterizing protein binding partners, including DNA, RNA, proteins, carbohydrates, organic molecules.
4. Characterizing binding partners including DNA, RNA, proteins, carbohydrates, organic molecules.
5. Characterizing binding of the components in a protein that participates in a multi-protein complex attached to the sensor.
6. Characterizing binding partners for a protein binding molecule attached to the sensor. Constructing a calibration curve for analyte using a set of analyte standards. Using the calibration curve to determine the analyte concentration in unknown solutions.
7. Identifying specific binding partners for single-stranded DNA or RNA attached to the sensor.
8. Single nucleotide polymorphism analysis.
9. Gas sensing (for example, an artificial "nose")
10. Measuring, monitoring, detecting and characterizing the deposition of thin films, in liquid, in air or in vacuum.
11. Measuring, monitoring, detecting and characterizing adsorption, moisture, particulate, contamination, bubble formation, surface oxidation, and corrosion in liquid, in a gaseous environment or in vacuum.
12. Detecting of virus capsids, bacteria, mammalian cells, biomembranes, biomaterials, self-assembled monolayers, molecularly imprinted polymers, langmuir-blodgett films, materials characterization and monitoring.

The invention claimed is:

1. A device for detecting and monitoring an oscillation of an analyte in a sample, comprising:
   (a) a first optical element having a transparent material and a first reflecting surface;
   (b) a second optical element positioned proximate to said first optical element and having a second reflecting surface free to deflect in response to a driving force and capable of oscillation over a range of frequencies;
   (c) a driving means controlled by a signal processor that generates a driving force to deflect said second reflecting surface;
   (d) an optical interferometer that senses deflections of said second reflecting surface by monitoring interference between light reflected from said first reflecting surface and light reflected from said second reflected surface;
   (e) an analyte-binding layer immobilized on said second reflecting surface; and
   (f) said signal processor that monitors oscillations of said second reflecting surface sensed by said optical interferometer,
   wherein said oscillations of said second reflecting surface in response to said driving force vary with analyte binding to said analyte-binding layer.

2. The device of claim 1, wherein said driving means is an external transducer.

3. The device of claim 1, wherein said driving means is integrated into the device.

4. The device of claim 1, wherein said driving force is an electrostatic force.

5. The device of claim 1, wherein the driving means includes a transducer capable of generating acoustic or ultrasonic pressure waves.

6. The device of claim 1, wherein said second surface includes a film including a magnetized material disposed on at least one side of said second surface.

7. The device of claim 1, wherein the driving means comprises:
- a signal source; and
- a magnetic field generator that generates a magnetic field directed toward said second surface and which is driven by said signal source.

8. The device of claim 1, wherein said second surface is electrically conductive.

9. The device of claim 1, wherein said driving means comprises:
- a signal source generating a current in said second surface; and
- a magnetic field generator,
- wherein said magnetic field generates a force on the current in said second surface causing a deflection of said second surface.

10. The device of claim 1, wherein said signal processor includes a synchronous detector with the signal from said optical sensor monitoring second surface deflections as input and the signal from the driving means as reference.

11. The device of claim 1, wherein said optical sensor is an optical interferometer comprising:
- a light source emitting light directed to said second surface;
- a photodetector capable of monitoring an optical interference signal; and
- a second surface capable of partially reflecting light;
- wherein said second surface is capable of partially reflecting light to the photodetector;
- wherein the deflection of said first surface changes the optical intensity at the photodetector to produce the optical interference signal.

12. The device of claim 1, wherein said second surface is a thin circular membrane held in tension.

13. The device of claim 1, wherein the optical sensor monitors changes in the amplitude of deflection of said second surface.

14. The device of claim 1, wherein the optical sensor monitors changes in the phase of the deflection of said second surface relative to the phase of the driving force.

15. The device of claim 1, wherein the driving means operates in a pulsed mode and the dissipation of the oscillation of said second surface is monitored.

16. The device of claim 1, wherein said second surface includes a layer of analyte binding molecules.

17. The device of claim 1, operating to detect specific molecular binding of at least one analyte to said second surface.

18. The device of claim 1, wherein the sample is a fluid.

* * * * *